(12) United States Patent
Sepehri et al.

(10) Patent No.: US 8,649,854 B2
(45) Date of Patent: Feb. 11, 2014

(54) METHOD AND DEVICE FOR THE DETERMINATION OF MURMUR FREQUENCY BAND

(75) Inventors: Amir A. Sepehri, Mons (BE); Arash Gharehbaghi, Tehran (IR)

(73) Assignee: Capis SPRL, Mons (BE)

( * ) Notice: Subject to any disclaimer, the term of this patent is extended or adjusted under 35 U.S.C. 154(b) by 521 days.

(21) Appl. No.: 12/866,139

(22) PCT Filed: Feb. 6, 2009

(86) PCT No.: PCT/EP2009/051410
§ 371 (c)(1),
(2), (4) Date: Oct. 6, 2010

(87) PCT Pub. No.: WO2009/098312
PCT Pub. Date: Aug. 13, 2009

(65) Prior Publication Data
US 2011/0021939 A1    Jan. 27, 2011

Related U.S. Application Data

(60) Provisional application No. 61/026,703, filed on Feb. 6, 2008.

(51) Int. Cl.
*A61B 7/04*    (2006.01)
(52) U.S. Cl.
USPC ............................................. 600/523
(58) Field of Classification Search
USPC ............................................. 600/528
See application file for complete search history.

(56) References Cited

U.S. PATENT DOCUMENTS

| 5,218,969 | A  |   | 6/1993  | Bredesen et al. |
| 5,638,823 | A  |   | 6/1997  | Akay et al. |
| 2004/0260188 | A1 |   | 12/2004 | Syed et al. |
| 2005/0222515 | A1 |   | 10/2005 | Polyshchuk et al. |
| 2006/0142667 | A1 | * | 6/2006  | Munk ............................ 600/528 |

FOREIGN PATENT DOCUMENTS

EP         1158145 A2    11/2001
WO    WO 2008/000259 A2    1/2008

OTHER PUBLICATIONS

Curt G. Degroff et al.; "Artificial Neural Network-Based ..."; journal publication; 2001, 6 pages, pp. 2711-2716.
Jacques P. De Vos et al.; "Automated Pediatric Cardiac Auscultation"; publication; Feb. 2007; 9 pages; pp. 244-252; IEEE Transactions on Biomedical Engineering, vol. 54, No. 2, Feb. 2007.
Sanjay R. Bhatikar et al., "A classifier based on the artificial neural network . . . "; publication; Jul. 24, 2004; 10 pages; pp. 251-260; Artificial Intelligence in Medicine (2005) 33, 251-260.

* cited by examiner

*Primary Examiner* — Christopher D Koharski
*Assistant Examiner* — Jeremiah Kimball
(74) *Attorney, Agent, or Firm* — Reinhart Boerner Van Deuren P.C.

(57) ABSTRACT

The present invention is related to a method for the determination of frequency band characteristics of a heart disease. A first set of phonocardiograms are recorded from a first set of reference healthy patients, and a second set of phonocardiograms from a second set of patients suffering of a heart disease. Spectral energies of all possible frequency bands are then calculated. These spectral energies are then compared in order to determine an optimized frequency band that gives rise to the maximal distinction between spectral energies of the phonocardiograms from first and second set of phonocardiograms.

14 Claims, 5 Drawing Sheets

METHOD AND DEVICE FOR THE DETERMINATION OF MURMUR FREQUENCY BAND

CROSS-REFERENCE TO RELATED APPLICATIONS

This patent application is the National Stage of International Application No. PCT/EP2009/051410, filed Feb. 6, 2009, that claims the benefit of U.S. Provisional Application No. 61/026,703, filed Feb. 6, 2008, the entire teachings and disclosure of which are incorporated herein by reference thereto.

FIELD OF THE INVENTION

The present invention is related to a method and a device for the determination of heart murmur frequency bands for categorizing pathological heart murmurs.

STATE OF THE ART

Around one percent of all children show some symptoms of congenital heart diseases. It is sometimes vital that the conditions of these children be screened before the age of twelve. While heart sound auscultation by an experienced physician is the primary and normal approach for screening of such conditions, shortage of experienced physicians, especially in the developing world, makes the automated screening approaches a priority. Some researches have been done on adult heart diagnosis by digital heart sound analysis method. However, this is only true to a lower extent for screening the children with congenital heart diseases. There are major differences in computerized verification of adult heart problems and screening congenital heart diseases in children.

The computerized phonocardiogram, as a noninvasive acoustical system for screening congenital heart diseases is a helpful tool for physicians. It can also open the way for verification of children heart states through telemedicine. It is worth noting that while digital phonocardiogram, alone, might not provide all the information needed to, e.g., make a decision on whether a heart surgery operation is advisable, it can drastically reduce unnecessary use of echocardiography, which is by far a more expensive and time-consuming tool. Furthermore, early diagnosis of heart defects in children may eliminate the need for later surgery operations altogether, provided that appropriate medical treatments are administered.

TABLE 1 frequencies of occurrences of cardiac malformation in 1000 children

| Malformation | Congenital heart disease % |
| --- | --- |
| Ventricular Septal Disease (VSD) | 33 |
| Patent Ductus Arteriosus (PDA) | 10 |
| Pulmonary valve Stenosis (PS) | 10 |
| Tetralogy of Fallot (TOF) | 9 |
| Aortic Stenosis (AS) | 8 |
| Atrial Septal Defect (ASD) | 5 |
| Coarction of Aorta | 5 |
| Transposition of great arteries | 5 |
| Atrioventricular septal defect | 4 |
| Truncus Ateriosus | 1 |
| Tricuspid atresia | 1 |
| Total anomalous pulmonary venous connection | 1 |
| Other | 8 |

Table 1 shows the occurrence frequencies of major cardiac malformations in children, as reported in "The heart: Congenital heart disease, in Basic Pathology", Chap. 11 (W. B. Saunders Company, Philadelphia USA, 1997).

The phonocardiogram (PCG), signal is a recording of acoustical waves caused by mechanical action of a heart and is semi-periodic. The electrocardiogram (ECG), signal is a recording of electrical potential initiated from electrical activities of heart cells. Normal heart sound contains two basic sound segments called S1 and S2 in each cycle. Mechanical activities of heart are always originated from electrical activity of heart. S1 always follows Q peak of ECG signal, while S2 follows its T peak.

EP 1558145 discloses a procedure for extracting information from heart sound signal. This document describes a procedure to extract murmur information from phonocardiographic data wherein time/frequency characteristics are used to detect heart sound features. More specifically, the signal is decomposed in both time and frequency slices, and systoles and diasystoles needs to be identified in order to use this method.

US 2005/0222515 discloses a method for defining heart sound signature from time-frequency distribution of heart sound energy. This document proposes a representation of said signature for the fast recognition of features by trained physicians.

U.S. Pat. No. 5,638,823 discloses the uses of time-frequency analysis to detect a risk factor for a patient of suffering of arterial stenosis.

Documents "Automated Pediatric Auscultation", J. P. de Vos et Al. in IEEE TRANSACTIONS ON BIOMEDICAL ENGINEERING, VOL. 54, NO. 2, FEBRUARY 2007 and "Artificial Neural Network-Based Method for Screening Heart Murmurs in Children", C. Degroff et Al. in Circulation, pp. 2712-2716, June 2001 disclose automated screening of congenital heart diseases that rely on wavelet analysis as the mathematical basis for feature extraction, ignoring the defective heart parts that cause the abnormality in the heart sound.

It is worth noting that every congenital heart disease causes abnormal heart sounds in a particular frequency band, which may not comply with the frequency-scales of the wavelet analysis. As a result, wavelet-based methods need to process the heart sound in multi-scales to allow for sufficient distinction between the normal and abnormal cases. This, however, increases the dimension of the feature vector, which in turn puts a negative impact on the quality of the classifier's test phase, assuming a fixed size of training data.

In addition, increase of the dimension of the feature vector may incorporate frequency bands into the classification process that are irrelevant. To make this point more clear, we note that some children with normal hearts might have innocent murmurs which have energy contents at frequencies close to those indicative of various heart diseases.

AIMS OF THE INVENTION

The present invention aims at providing a method and an associated device for detecting heart pathology from a phonocardiogram that do not present the drawbacks of the state of the art.

The present invention further aims to provide a method and an associated devise for determining frequency bands that can be used for defining a feature vector for a detection of heart murmur, and a related heart pathology.

SUMMARY OF THE INVENTION

A first aspect of the invention is related to a method (not applied upon a mammal (including a human) body) for a determination of frequency band characteristics of a heart disease comprising the steps of:

collecting and/or recording (from a data base) a first set of phonocardiograms from a first set of reference healthy patients, and a second set of phonocardiograms from a second set of patients suffering of this heart disease;

defining a frequency sampling rate, and a maximum cutoff frequency, producing a finite set of sampled frequencies;

calculating spectral energies at all sampled frequencies;

calculating spectral energies of all possible frequency bands;

comparing these spectral energies of all possible frequency bands;

determining a frequency band giving for rise to a maximal distinction between spectral energies of these phonocardiograms from a first and a second set of phonocardiograms. In this method, the (maximal) Cut-Off frequency is of about 500 Hz (preferably at a value comprised between about 400 Hz and about 600 Hz).

By frequency band, it is meant, in the present document, a particular frequency interval, delimited by particular sampled frequencies.

In a second aspect, the present invention is related to a method for a detection of heart diseases affecting a patient which, in addition to a determination of frequency band characteristics of a heart disease, comprises the steps of comparing this optimized frequency band energy of phonocardiograms of a particular patient to a corresponding frequency band energy of a first and a second set of phonocardiograms to define if this (particular) patient suffers of this (particular) heart disease.

According to a preferred embodiment of present invention, this method is further characterised by one or a suitable combination of the following features:

the heart disease is preferably selected from the group consisting of ventricular septal defect, patent ductus arteriosus, pulmonary valve stenosis, tetralogy of fallot, aortic stenosis, atrial septal defect, coarctation of aorta, transposition of great arteries, atrioventricular septal defect, truncus arteriosus, tricuspid atresia, anomalous pulmonary pulmonary venous connection or a mixture thereof;

the frequency band determination range is comprised between about 1 Hz and about 500 Hz;

the determined frequency band is comprised between about 88 Hz and about 96 Hz and the heart disease is ventricular septal defect;

the determined frequency band is comprised between about 50 Hz and about 60 Hz and the heart disease is tetralogy of fallot;

the determined frequency band is comprised between about 15 Hz and about 121H, and the heart disease is ventricular patent ductus arteriosus;

the determined frequency band is comprised between about 17 Hz and about 129 Hz and the heart disease is aortic stenosis;

the determined frequency band is comprised between about 16 Hz and about 32 Hz and the heart disease is pulmonary valve stenosis;

the spectral energies are calculated only on the systolic segment of the phonocardiogram and/or the comparison between phonocardiograms is performed by a neural network.

Another aspect of the invention is related to a device comprising phonocardiogram(s) recording media, phonocardiogram(s) storage media, output media, a processor and a set of instructions for performing the method according to the invention.

The invention is also related to a set of instructions executable on a programmable device, which when executed, performs the described method.

BRIEF DESCRIPTION OF THE DRAWINGS

FIG. 6 is representing PCG and ECG of a twelve year boy with AS.

The outputs of the algorithm according to the Jack-Knife validation. Abnormal cases (patients 1-54) are denoted by ($\Diamond$) and normal cases (patients 55-90) are denoted by ( ).

DETAILED DESCRIPTION OF THE INVENTION

The present invention discloses a method for automated screening congenital heart diseases in children through heart sound analysis techniques.

The method relies on categorizing the pathological murmurs based on the heart sections initiating the murmurs. These pathological murmur categories can be identified by examining the heart sound energy over specific frequency bands, which will be referred hereafter as Arash-Bands.

Depending on the type of heart defect, murmurs may appear in different segments of the heart sound. However, most frequently observed diseases cause some kind of murmur in the systolic segments. Therefore, it is preferred to use the systolic segments of the heart sound for diagnosis.

For determining the Arash-Bands for each category, the energy of the heart sound is evaluated over all possible frequency bands. The Arash-Band is then defined as the band that provides the lowest clustering error as compared to the normal heart sound. The energy content of the Arash-Bands then constitutes a feature vector suitable for classification using a neural network.

The approach of the present invention in determining the Arash-Band for each disease is such that the energy contents of the heart sound over the Arash-Band for a disease provides the maximal distinction between normal and the abnormal cases. A Multi Layer Perceptron (MLP) neural network is advantageously to classify the feature vectors constructed from the Arash-Band energies to normal and abnormal cases.

A multilayer perceptron is a feedforward artificial neural network model that maps sets of input data onto a set of appropriate output. It is a modification of the standard linear perceptron in that it uses three or more layers of neurons (nodes) with nonlinear activation functions, and is more powerful than the perceptron, because it can advantageously distinguish data that is not linearly separable, or separable by a hyperplane.

Accurate specification of the Arash Bands, through the minimization of the feature vector dimension, makes the classifier more robust against possible false diagnosis (positive or negative) for such cases.

The proposed screening method relies on classification of congenital heart diseases based on the heart parts that cause the pathological murmurs, rather than standard medical classifications.

It was found that the heart sound of children with congenital heart diseases shows energy concentrations over specific frequency bands that are different from those of the normal children. These frequency bands are called Arash-Bands.

The spectral energies of the Arash-Bands can thus be used as a feature vector to screen congenital heart diseases in children. These Arash-Bands depend on the heart sections causing the murmurs.

Some of the congenital heart diseases make murmurs which are not corresponding to the defective heart sections. There are also congenital heart diseases where the murmurs are produced by the same heart sections (e.g., ASD and PS diseases). The murmurs in ASD and PS diseases are caused by the overflow of the pulmonary valve. As will be shown, the Arash-Bands for these two diseases advantageously coincide, which confirms the link between Arash-Bands and the heart sections that initiate murmurs. The final disease screening is performed by a neural network that acts upon a feature vector constructed from the energy contents of the Arash-Bands for all the diseases of interest.

The Arash-Band for a specific congenital heart disease is the frequency band that provides the maximal distinction between the spectral energy of the normal and abnormal heart-sounds. To determine the Arash-Band, the power spectral density function (PSD) is used.

The analysis of the spectral energy distribution, for all available phonocardiogram, indicates that heart sound signal has a negligible energy for frequencies above 500 Hz (Fmax).

Therefore, it is preferred to limit the sound analysis to about 500 Hz.

In a first step, spectral energy over all possible frequency bands is calculated for all the cases in the training data-bank. With indices $k=1, \ldots, N$ (N is the total number of sub-bands) assigned to all possible sub-bands below the Fmax, the energy of the sub-band k between the two arbitrary frequencies f1 and f2 is computed as:

$$E(k) = \sum_{f=f_1}^{f_2} PSD(f)$$

where PSD(f) is the power spectral density function of the signal.

If f1=0 and the frequency f2 is increased by 1 Hz steps (f2=1, ..., Fmax), all possible sub-band energies starting with f1=0 are calculated as follow:

$$E(k) = \sum_{f_2=1}^{F_{max}} \sum_{f=0}^{f_2} PSD(f)$$

$$k = f_2$$

In this case $k=1, \ldots, Fmax$ and the total number of all possible sub-bands is Fmax.

If f1=1 is assumed, then f2=2, ..., Fmax and sub-band energies are:

$$E(k) = \sum_{f_2=2}^{F_{max}} \sum_{f=1}^{f_2} PSD(f)$$

$$k = F_{max} + f_2 - 1$$

In this case $k=(Fmax+1), \ldots, (2*Fmax-1)$ which begins right after the previous case (k=Fmax) and the total number of all possible frequency bands is (Fmax-1).

As the f1 increases by one, the total number of the k decreases by one. The sub-band indices k, for each case of f1, should not overlap with the previous case. If $f1=0, \ldots$, (Fmax-1), computing all sub-band energies for each f1 determines all possible sub-band energies below the frequency Fmax.

More generally, the following relations formulate sub-band energies computation:

$$E(k) = \sum_{f_1=0}^{F_{max}-1} \sum_{f_2=f_1+1}^{F_{max}} \sum_{f=f_1}^{f_2} PSD(f) \quad \text{Eq. 1}$$

$$k = F_{max} * f_1 - \sum_{j=0}^{f_1} j + f_2 \quad \text{Eq. 2}$$

where k covers all possible sub-bands below the frequency Fmax. The total number of sub-bands is $$N = \frac{F_{max} * (F_{max} + 1)}{2}.$$

The Arash-band for a congenital heart disease is the frequency band with maximum spectral energy differences between the defected heart sounds and normal ones. The determination of the Arash-band then comprises the following steps:

define $E_{l,i}(k)$ to sub-band energy of a heart sound signal for the subject l in the class i for a specified sub-band k;

assign a discriminating threshold between the two classes for each $E_{l,i}(k)$ with respect to k;

determine the mean value and the variance of $E_{l,i}(k)$ for the two classes (i=1, 2) for finding the thresholds:

$$\mu_i(k) = \frac{1}{N_i} \sum_{l=1}^{N_i} E_{l,i}(k) \quad \text{Eq. 3}$$

$$\delta_i^2(k) = \frac{1}{N_i} \sum_{l=1}^{N_i} (E_{l,i}(k) - \mu_i(k))^2 \quad \text{Eq. 4}$$

$$k = 1, \ldots, N \text{ and } i = 1, 2$$

where $\mu_i(k)$ represents mean value of a sub-band energy k, for normal (i=1) and a congenital heart disease (i=2), represents variance value of a sub-band energy k, for normal (i=1), and a congenital heart disease (i=2), N denotes the number of all possible sub-band, Ni represents the number of cases in the data-bank.

Optionally, the two classes (normal/abnormal) can be considered as one and are later on clustered with a selected thresholds, in order to extract the bands with maximum energy difference between the two classes.

The determination of the discriminating threshold for sub-band k, is calculated by:

$$T(k) = \frac{\delta_i^2(k) \cdot \mu_2(k) + \delta_i^2(k) \cdot \mu_1(k)}{\delta_i^2(k) + \delta_i^2(k)} \quad \text{Eq. 5}$$

d(k), has a value with tendency toward the group with smaller variance.

The error er(k), between the clusters for each sub-band k are:

$$er_i(k) = \sum_{l=1}^{N_i} (\text{sgn}((\mu_i(k) > d(k)) \wedge (E_i(l) < d(k))) + \quad \text{Eq. 6}$$

$$\ldots \ldots + \text{sgn}((\mu_i(k) < d(k)) \wedge (E_i(l) > d(k))))$$

$$er(k) = \sum_{i=1}^{2} er_i(k) \quad \text{Eq. 7}$$

where, sgn(t) is a boolean function and defined as:

$$\text{sgn}(t) = \begin{cases} 1 & t =' true' \\ 0 & t =' false' \end{cases} \quad \text{Eq. 8}$$

Among the selected bands with the same minimum errors, the optimum one is selected by using classic scattering formula for each selected frequency band k, as:

$$S(k) = \frac{|\mu_1(k) - \mu_2(k)|}{\delta_i^2(k) + \delta_i^2(k)} \quad \text{Eq. 9}$$

The optimum frequency band is then the band which results in the largest S(k).

$$K_{opt} = \arg_k \max S(k) \quad \text{Eq. 10}$$

Instead of using S(k) parameter, one can take advantage of statistical distribution of frequency band energies with the least errors.

the determined Arash-Bands also provides the means for implementation of a smart stethoscope, which could be used for automated screening of patients such as children for congenital heart diseases, possibly via means using internet or telemedicine.

DESCRIPTION OF A PREFERRED
EMBODIMENT OF THE INVENTION

As it is shown in table 1, six diseases named VSD, ASD, PDA, TOF, PS and AS constitute more than 75% of all congenital heart diseases. These congenital heart diseases were therefore chosen as case-studies to demonstrate how the person skilled in the art can use the method of the invention.

The method for a determination of frequency band was applied on 40 subjects (human patients) presenting normal and abnormal signals in training phase. Then the heart disease detection method was used with 50 subjects (human patients) presenting normal and abnormal cases out of training signals. The result of more than 94% correct classification shows that the method of the invention is efficient in screening of patients, especially children with congenital heart diseases. In order to have a better prediction of the invention method performance with a larger number of data, the Jack-Knife validation method was applied on 90 available subjects (phonocardiograms) and achieved 100% of accuracy.

PCG and ECG signals from ninety children were collected. Forty of these signals were used as training data-bank, and the remaining fifty signals were used as test data-bank. From the forty training signals, twenty-four are from children with VSD, ASD, PDA, TOF, PS and AS diseases (four signals per each disease). The remaining sixteen training signals are from children with normal PCG or with innocent murmurs. From the fifty test signals, thirty are from children with heart diseases (five signal per disease), and the remaining twenty signals are normal PCG.

The signals in this data-bank were collected under the supervision of pediatric cardiologists, and using echocardiography and complementary tests courtesy of Teheran Children Heart Center. All PCG and ECG signals were recorded over a time-interval of ten seconds. A WelchAllyn Meditron stethoscope and ECG were used. For data acquisition, a 1.8 GHz ACER notebook with a 16 bit stereo soundcard and sampling rate 44.1 KHz was used.

Applying the procedure on each congenital heart disease group with respect to the normal group, six optimized frequency bands were obtained. The Arash-Bands (in Hz) determined by the method previously described, with the available set of data for each congenital heart disease are:

WVSD=88-96

WTOF=50-60

WPDA=15-121

WAS=17-129

WASD=17-33

WPS=16-32

As it is observed the two bands (WASD, WPS) are almost overlapped. As it was mentioned in section 2, the murmurs for the ASD and the PS are originated by the same heart section.

A neural network classifier have been used for distinguishing between children with heart defects and the normal children. Since the two frequency bands, WASD and WPS have a great overlap with each other, the two frequency bands as WASDPS=16-33 were combined. The spectral energies of 5 Arash-Bands; WVSD, WTOF, WPDA, WAS and WASDPS serve as the feature vector for the heart sound classification.

A three layer MLP neural network was used to screen phonocardiograms from children with congenital heart disease. The neural network has 5, 10 and 1 neurons in its input, mid and output layers respectively with tangent sigmoid transfer function. The neural network has been trained with back propagation error method.

The training data-bank, as detailed in section 3, was used to train the algorithm including Arash-Band calculations and neural network learning.

To evaluate the performance the method of the present invention, the test data-bank, which was detailed in section 3 was used. The screening results were then compared against those performed by pediatric cardiologists who used echocardiography in conjunction with other complementary tests as the golden standards for their diagnosis.

Table 2 shows the results of this comparison.

TABLE 2

The algorithm outputs for the test data-bank against the cardiologist's diagnosis

| The Algorithm | Cardiologist | |
| --- | --- | --- |
|  | Normal | Abnormal |
| Normal | 19 | 2 |
| Abnormal | 1 | 28 |

The following three criteria were used as benchmarks for the invention method:
false Negative Error (F. N.): Normal diagnosis for abnormal cases over the total number of abnormal cases;
false Positive Error (F. P.): Abnormal diagnosis for normal cases over the total number of normal cases;
efficiency: Total false diagnosis over the total number of cases.

Table 3 shows the result of our method according to the above criteria:

TABLE 3

Result of screening children congenital heart disease on the test data bank of 50 cases

| Normal | Abnormal | F.P. (%) | F.N. (%) | Efficiency (%) |
| --- | --- | --- | --- | --- |
| 20 | 30 | 5 | 6.67 | 94 |

As can be seen from table 3, the efficiency of the method with the given set of data is more than ninety-four percent, which is significant.

Figure 1:
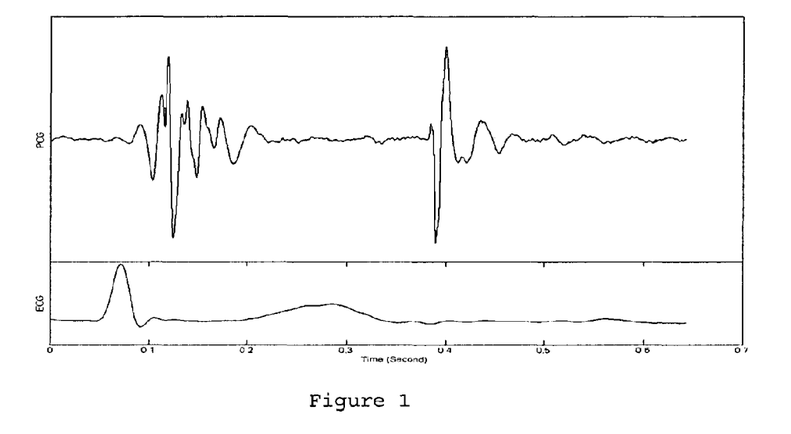
FIG. 1 is representing a complete heart sound cycle (top) along with ECG signal (bottom).
Figure 2:
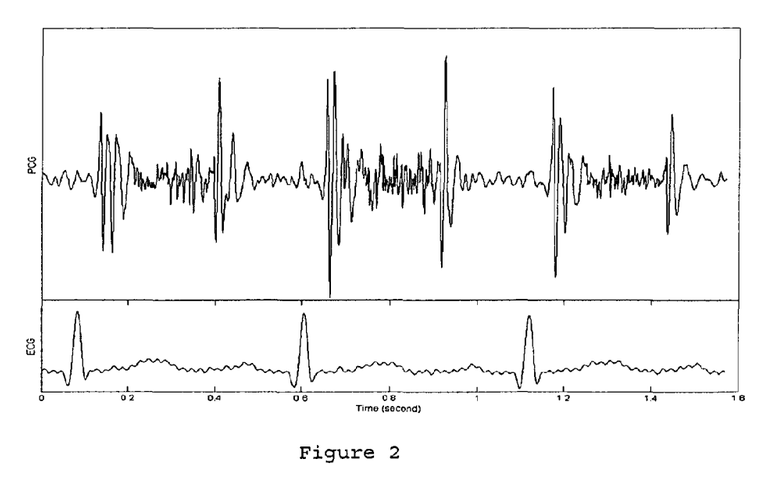
FIG. 2 is representing PCG and ECG of a three year girl with VSD.
Figure 3:
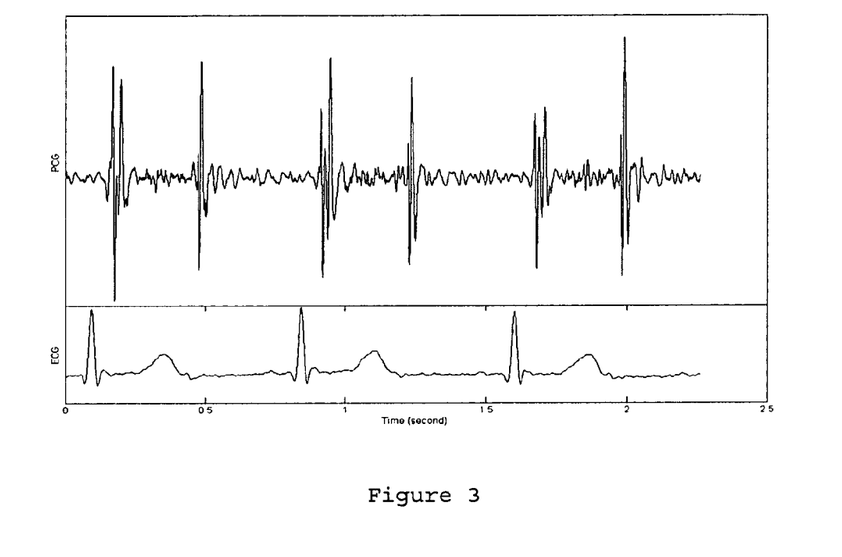
FIG. 3 is representing PCG and ECG of a six month girl with PDA.
Figure 4:
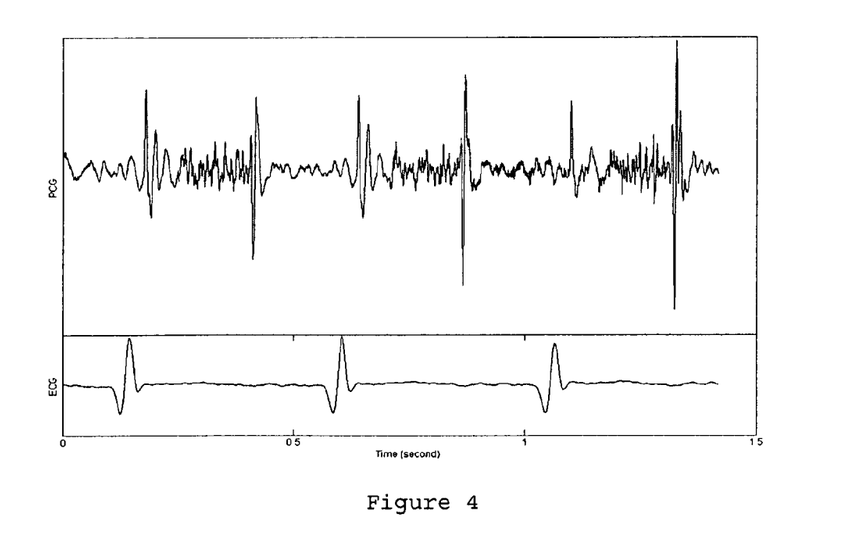
FIG. 4 is representing PCG and ECG of a three month boy with PS.
Figure 5:
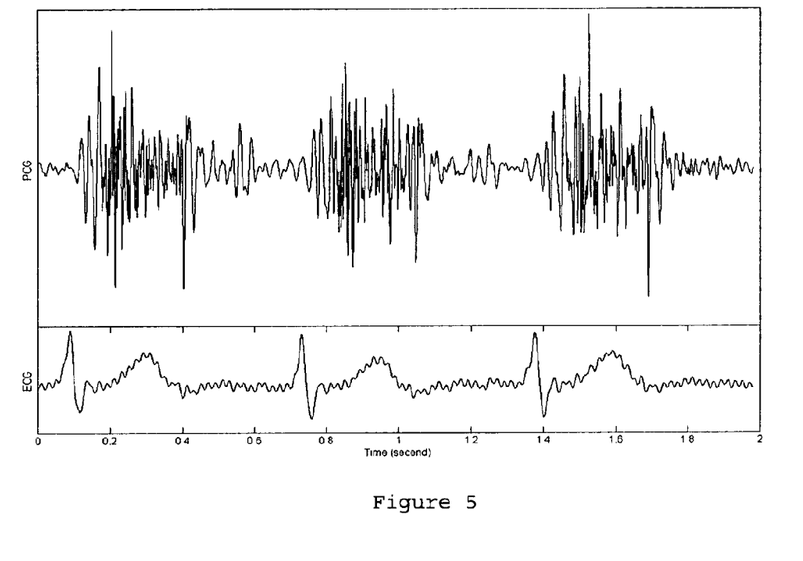
FIG. 5 is representing PCG and ECG of a two year boy with TOF.
Figure 6:
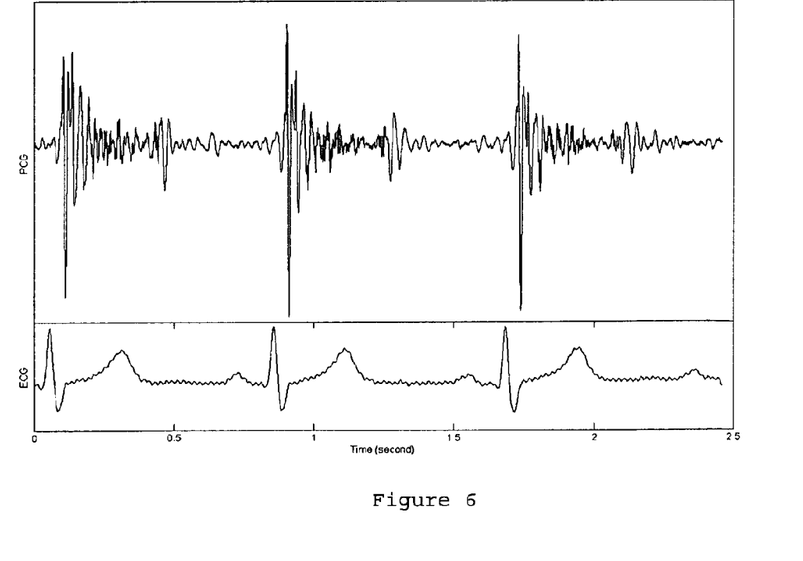
Figure 7:
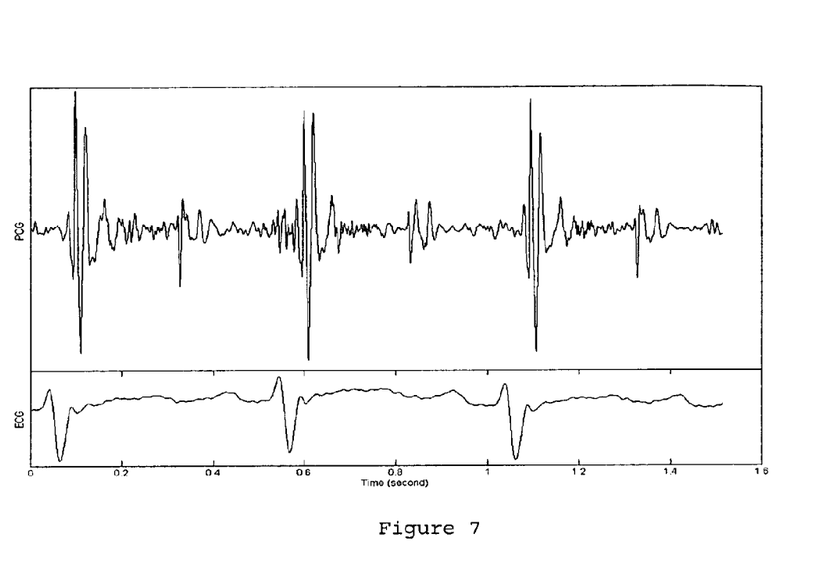
FIG. 7 is representing PCG and ECG of a six year boy with ASD.
Figure 8:
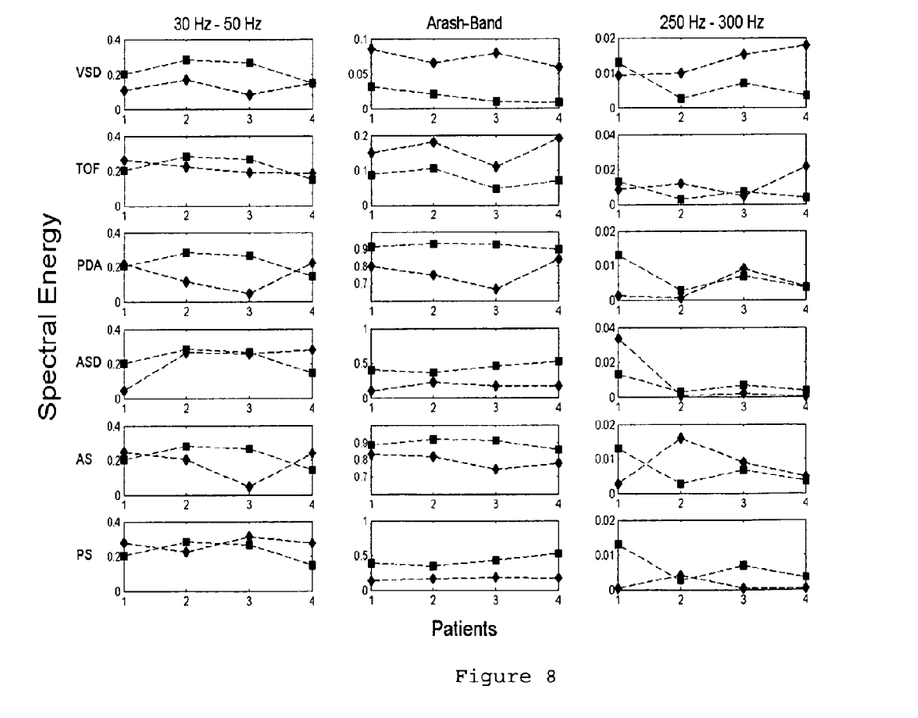
FIG. 8 is representing The spectral energy, calculated for two arbitrary frequency bands (30 Hz-50 Hz, 250 Hz-300 Hz) along with Arash-Band for 4 cases of each children congenital heart diseases VSD, TOF, PDA, ASD, AS and PS ($\Diamond$) against the normal cases ( ). It is easily seen that the discrimination of normal cases from defect ones is much better for Arash-Band energies.

The Arash-Band for a congenital heart disease is a frequency band whose energy content provides the maximal distinction between the normal and abnormal cases. To demonstrate this, the inventors have calculated the energy of Arash-Bands, along with those of two other arbitrary bands, for the four instances of each of the six diseases in the training data base and plotted them against the energy contents for the normal cases (FIG. 8). It is easily seen from FIG. 8 that the Arash-Band, as compared to the other two bands, provides a much better basis for distinction between the normal and abnormal cases.

Figure 9:
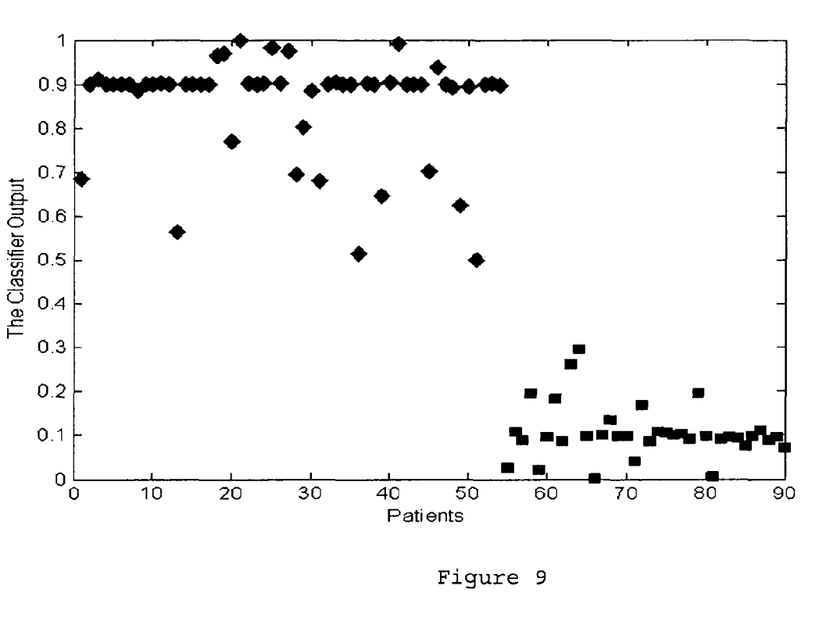

In order to have a better validation of the output, the Jack-Knife method was used. In this method, a data is taken off the data base and the rest is used to train the neural network. The excluded data is then used to evaluate (and validate) the output. This is repeated until all data in the data base is validated. FIG. 9 shows the output of the proposed method for the data-bank, using the Jack-Knife method.

As FIG. 9 shows the false negative and false positive errors are both zero according to this validation.

Therefore, the Arash-Bands energies of the four diseases constitute suitable feature vectors for screening of congenital heart diseases in children through a MLP neural network.

The determined Arash-Bands is also useful in distinguishing pathological murmurs from innocent ones.

What is claimed is:

1. A method for a determination of frequency band characteristic of a heart disease comprising the steps of:
using an electronic stethoscope, collecting and/or recording a first set of phonocardiograms from a first set of reference healthy patients, and a second set of phonocardiograms from a second set of patients suffering of said heart disease;
defining a frequency sampling rate and a maximum cutoff frequency, producing a finite set of sampled frequencies;
calculating spectral energies at all sampled frequencies, said spectral energies being calculated on the entire phonocardiogram;
calculating spectral energies of all possible frequency bands by summing spectral energies at sample frequencies belonging to said frequency bands;
comparing said spectral energies of all possible frequency bands; and
determining a frequency band giving rise to a maximal distinction between spectral energies of the said phonocardiograms from the first and the second set of phonocardiograms.

2. A method for a detection of heart diseases comprising the steps of:
determining frequency band giving rise to a maximal distinction between spectral energies of the said phonocardiograms from the first and the second set of phonocardiograms by using the method of claim 1; and
comparing said determined frequency band energy of phonocardiograms of a patient to corresponding frequency band energy of the first and the second set of phonocardiograms to define if said patient suffers of the heart disease.

3. The method according to claim 1 wherein the heart disease is selected from the group consisting of ventricular septal defect, patent ductus arteriosus, pulmonary valve stenosis, tetralogy of fallot, aortic stenosis, atrial septal defect, coarctation of aorta, transposition of great arteries, atrioventricular septal defect, truncus arteriosus, tricuspid atresia, anomalous pulmonary venous connection or a mixture thereof.

4. The method according to claim 1 wherein the maximum cutoff frequency is about 500 Hz.

5. The method according to claim 2 wherein the determined frequency band is comprised of between 88 Hz and 96 Hz and the heart disease is ventricular septal defect.

6. The method according to claim 2 wherein the determined frequency band is comprised of between 50 Hz and 60 Hz and the heart disease is tetralogy of fallot.

7. The method according to claim 2 wherein the determined frequency band is comprised of between 15 Hz and 121 Hz and the heart disease is ventricular patent ductus arteriosus.

8. The method according to claim 2 wherein the determined frequency band is comprised of between 17 Hz and 129 Hz and the heart disease is aortic stenosis.

9. The method according to claim 2 wherein the determined frequency band is comprised of between 16 Hz and 32 Hz and the heart disease is pulmonary valve stenosis.

10. The method according to claim 1 wherein the spectral energies are calculated only in the systolic segment of the phonocardiogram.

11. The method according to claim 1 wherein the comparison between phonocardiograms is performed by a neural network.

12. The method according to claim 11 wherein the neural network is of multilayer perceptron type.

13. A device comprising non-transitory phonocardiogram(s) recording media, non-transitory phonocardiogram(s) storage media, non-transitory output media, a processor and a set of instructions for performing the method according claim 1.

14. A set of instructions, on a non-transitory computer readable medium, executable on a programmable device, which when executed on said programmable device, performs the method according to claim 1.

\* \* \* \* \*